United States Patent
Beyar

(10) Patent No.: US 6,726,675 B1
(45) Date of Patent: Apr. 27, 2004

(54) REMOTE CONTROL CATHETERIZATION

(75) Inventor: Dalia Beyar, Haifa (IL)

(73) Assignee: Navicath Ltd., Nesher (IL)

( * ) Notice: Subject to any disclaimer, the term of this patent is extended or adjusted under 35 U.S.C. 154(b) by 0 days.

(21) Appl. No.: 09/623,900

(22) PCT Filed: Mar. 9, 1999

(86) PCT No.: PCT/IL99/00136

§ 371 (c)(1),
(2), (4) Date: Dec. 12, 2000

(87) PCT Pub. No.: WO99/45994

PCT Pub. Date: Sep. 16, 1999

(30) Foreign Application Priority Data

Mar. 11, 1998 (IL) .................................................. 123646

(51) Int. Cl.$^7$ ............................................. A61M 31/00
(52) U.S. Cl. ....................... 604/510; 604/528; 600/106; 600/114; 600/137
(58) Field of Search .............................. 604/95.01, 156, 604/500, 510, 523, 528, 164.12, 165.02; 600/101, 103, 106, 114, 117, 137, 424

(56) References Cited

U.S. PATENT DOCUMENTS

| | | |
|---|---|---|
| 5,351,676 A | 10/1994 | Putman |
| 5,377,678 A | 1/1995 | Dumoulin et al. |
| 5,396,880 A | 3/1995 | Kagan et al. |
| 5,423,321 A | 6/1995 | Fontenot |
| 5,484,407 A | 1/1996 | Osypka |
| 5,492,131 A | 2/1996 | Galel |
| 5,524,180 A | 6/1996 | Wang et al. |
| 5,540,649 A | 7/1996 | Bonnell |
| 5,586,968 A | * 12/1996 | Grundl et al. ............... 600/114 |
| 5,704,897 A | 1/1998 | Truppe |
| 5,728,044 A | 3/1998 | Shan |
| 5,741,271 A | 4/1998 | Nakao et al. |
| 5,779,623 A | 7/1998 | Bonnell |
| 6,358,199 B1 * | 3/2002 | Pauker et al. ............... 600/114 |

FOREIGN PATENT DOCUMENTS

| | | |
|---|---|---|
| DE | 285 6439 | 7/1980 |
| DE | 423 33 23 | 4/1994 |
| EP | 4 00 802 | 4/1990 |
| EP | 0 753 321 | 1/1997 |
| JP | 718 4923 | 7/1995 |
| SU | 279814 | 12/1968 |
| SU | 992067 | 1/1980 |
| SU | 992067 | 3/1981 |
| WO | WO 93 20876 | 10/1993 |
| WO | WO 95/02233 | 1/1995 |
| WO | WO 96/21486 | 3/1995 |

OTHER PUBLICATIONS

Medline 923139466: Wu, J.R et al, "An Investigation of Radiation Exposure on Pediatric Patients and Doctors During Cardiac Catheterization and Cineangiography", *Journal of Medical Sciences*, 1991, Sep. 7 (9), pp. 448–453, abstract.

Embase 79213961: Biazzi, L. et al, "Radiation Exposure and Protection During Angiograph", *Ann. Radiol.*, 1979, Apr. 22, pp. 345–347, abstract.

Embase 79213959: Essinger A. et al, "Radiation Exposure to the Examiner During Coronary Angiograph", *Ann. Radiol.*, 1979, Apr. 22, pp. 340–343, abstract.

(List continued on next page.)

*Primary Examiner*—LoAn H. Thanh
*Assistant Examiner*—Jeremy Thissell
(74) *Attorney, Agent, or Firm*—Hoffman, Wasson & Gitler, PC

(57) ABSTRACT

A remote control catheterization system (20) includes a propelling device (28), which controllably inserts a flexible, elongate probe (26) into the body of a patient (22). A control console (34), in communication with the propelling device, includes user controls (38, 40) which are operated by a user of the system remote from the patient to control insertion of the probe into the body by the propelling device.

26 Claims, 3 Drawing Sheets

OTHER PUBLICATIONS

Medline 94345145: Magnavita, N. et al., "Occupational Risk Caused by Ultrasound in Medicine", *Radiologia Medica*, 1994, Jul.–Aug., 88(1–2), pp. 107–111, abstract.

Healsafe 86:4120, Becker, Y., "Cancer in Ataxia–Telangiectasia Patients: Analysis of Factors Leading to Radiation Induced and Spontaneous Tumors", *Anticancer Res.*, 1986, vol. 6, No. 5, pp. 1021–1032, abstract.

Favaretti, C. et al., "The Distribution and Activities of Hemodynamic Laboratories in Italy: The Implications for the Quality of Services", *G. Ital. Cardiol.*, 1994, May, 24:5, pp. 477–482, abstract.

van den Brand, M., "Utilization of Coronary Angioplasty and Cost of Angioplasty Disposables in 14 Western European Countries; European Angioplasty Survey Group", *Eur. Heart J.*, 1993, Mar. 14:3, 391–7, abstract.

Roach, H. et al., "Intravenous Site Care Practices in Critical Care, A National Survey", *Heart Lung*, 1995, Sep.–Oct., 24:5, 420–4, abstract.

Embase 79213961: Biazzi, L. et al, "Radiation Exposure and Protection During Angiography", *Ann. Radiol.*, 1979, Apr. 22, pp. 345–347, abstract.

Embase 79213959: Essinger A. et al, "Radiation Expoosure to the Examiner During Coronary Angiography", *Ann. Radiol.*, 1979, Apr. 22, pp. 340–343, abstract.

Medline 94345145: Magnavita, N. et al., "Occupational Risk Caused by Ultrasound in Medicine", *Radiologia Medica*, 1994, Jul.–Aug., 88(1–2), pp. 107–111, abstract.

Healsafe 86:4120, Becker, Y., "Cancer in Ataxia–Telangiectasia Patients: Analysis of Factors Leading to Radiation Induced and Spontaneous Tumors", *Anticancer Res.*, 1986, vol. 6, No. 5, pp. 1021–1032, abstract.

van den Brand, M., "Utilization of Coronary Angioplasty and Cost of Angioplasty Disposables in 14 Western European Countries; European Angioplasty Survey Group", *Eur. Heart J.*, Mar. 14:3, 391–7, abstract.

Roach, H. et al., "Intravenous Site Care Practices in Critical Care, A National Survey", *Heart Lung*, 1995, Sep.–Oct., 24:5, 420–4, abstract.

* cited by examiner

REMOTE CONTROL CATHETERIZATION

FIELD OF THE INVENTION

The present invention relates generally to invasive medical probes and methods, and specifically to intravascular catheterization and catheterization techniques.

BACKGROUND OF THE INVENTION

Catheterization procedures are very commonly performed for diagnosis and treatment of diseases of the heart and vascular system. The catheterization procedure is generally initiated by inserting a guide wire into a blood vessel in the patient's body. The guide wire is then guided to the desired location, most commonly in one of the heart vessels or elsewhere in the vascular system. At this point the catheter is slid over the guide wire into the blood vessel and/or heart. Once the catheter is in the desired position, the guide wire can then be removed, leaving the catheter in location. Alternatively, in some procedures, the catheter is inserted without using a guide wire. The catheter may be used to pass ancillary devices into the body, such as an angioplasty balloon, or to perform other diagnostic or therapeutic procedures.

In order to facilitate the guide wire insertion and the subsequent catheter application, the physician generally performs the procedure with the assistance of a fluoroscope, as is well known in the art. The fluoroscope produces a real-time image showing the continued progress of the guide wire, or the catheter, through the patient's body.

The fluoroscope generates a high level of X-ray radiation, which poses a significant danger to medical personnel exposed thereto, as is well known in the art. In order to provide protection from radiation exposure, the attending medical personnel generally wear a heavy, cumbersome protective lead garment which covers the entire body and neck, or use various lead shields including transparent glass face and eye shields.

SUMMARY OF THE INVENTION

It is an object of some aspects of the present invention to provide apparatus and methods of catheterization that allow medical personnel to be distanced from the vicinity of the fluoroscope and its resultant radiation, thereby reducing radiation exposure of the personnel.

It is a further object of some aspects of the present invention to provide a mechanism for remote control performance of catheterization procedures.

In preferred embodiments of the present invention, a remote control catheterization system feeds an intravascular catheter into the body of a patient. The system is preferably used to perform substantially all aspects of a catheterization procedure, including insertion of a guide wire in preparation for catheter insertion and therapeutic and/or diagnostic treatments using the catheter. The system is operated by a physician who observes a fluoroscopic image of the procedure on a remote fluoroscope screen, preferably outside the room in which the patient is located, and controls the procedure using a remote control console.

In some preferred embodiments of the present invention, the physician inserts a cannula into the patient's blood vessel and inserts a guide wire through the cannula into the body, in a manner known in the art. The proximal portion of the guide wire is fed through a propelling device, which feeds the guide wire into the vessel while providing steering and speed control. The propelling device is controlled by the physician using the remote control console.

Once the guide wire has been inserted to a desired location, for example within a coronary artery, the physician passes a catheter over the proximal end of the guide wire. The proximal portion of the catheter is then placed in the propelling device, which feeds the catheter over the wire, similarly under the physician's control using the console. The feeding device may then be used similarly to control the catheter inside the body and to pass ancillary devices, such as an angioplasty balloon, through the catheter.

In some preferred embodiments of the present invention, the propelling device comprises one or more propelling mechanisms, preferably three such mechanisms, one for each of the guide wire, catheter and ancillary device. In one such preferred embodiment, each of the propelling mechanisms comprises two wheels, preferably fabricated from a rigid non-corrosive material, such as PVC. The distance between the wheels is adjustable to the accommodate the width of the guide wire, catheter or ancillary device, as applicable. The wheels are driven by a small motor, as is well known in the art, which is controlled by the physician using the remote control console.

Although it is most convenient to use three separate propelling mechanisms, in an alternative preferred embodiment of the present invention, the propelling device comprises only one propelling mechanism. The sole propelling mechanism comprises two adjustable wheels as described above, a motor, and applicable gauges. Once the guide wire has been inserted to a desired position within the body, the guide wire is removed from between the wheels of the propelling mechanism, and the catheter or ancillary device is threaded into the propelling mechanism, as applicable.

In other preferred embodiments of the present invention, the propelling mechanism may comprise a robot arm, or any other suitable manipulation mechanism known in the art.

In preferred embodiments of the present invention, the physician receives feedback, preferably both tactile and visual feedback, indicative of the force needed to insert the guide wire, catheter or ancillary device. This feedback alerts the physician if an obstruction or other obstacle has been encountered. In the preferred embodiment described above, torque gauges are preferably coupled to the motor to measure the reverse force applied to the guide wire, catheter or ancillary device during insertion, and thus provide the feedback. Additionally, a rotor gauge is preferably coupled to the guide wire, catheter or ancillary device to measure and verify its speed of advance.

Preferably, the torque gauges or other force-measuring devices are coupled to a safety mechanism, which halts the insertion if the gauge reaches a predetermined force threshold.

The torque measurement, along with the measured speed, are relayed to the remote console situated outside of the catheterization room. The physician at the console thereby has at his command substantially all the information needed to control the procedure: the fluoroscope display, the reverse force measurement, and the measurement of the advance speed. This information enables the physician to perform the guide wire insertion, as well as catheter insertion and other diagnostic or therapeutic procedures, as applicable, via remote control, substantially without exposure to X-ray radiation.

In some preferred embodiments of the present invention, the remote control console comprises a steering device, preferably a joystick. The speed and direction of motion of the propelling device are controlled by the direction and extent to which the physician displaced the joystick from its center, "zero" position. Preferably, the reverse force measurement is fed back to the joystick, so that the greater the resistance encountered by the guide wire, catheter or ancillary device, the greater is the force required to displace the joystick.

Although preferred embodiments are described herein with reference to cardiac catheterization procedures, it will be appreciated that the principles of the present invention may similarly be applied to other medical procedures that are performed using fluoroscopic visualization, for example, non-cardiac catheterization or angioplasty, and other radiological procedures involving the use of catheters under fluoroscopy.

There is therefore provided, in accordance with a preferred embodiment of the present invention, a remote control catheterization system including:

a propelling device, which controllably inserts a flexible, elongate probe into the body of a patient; and a control console, in communication with the propelling device, and including user controls which are operated by a user of the system remote from the patient to control insertion of the probe into the body by the propelling device.

Preferably, the propelling device includes wheels which roll against the elongate probe in one direction to advance the elongate probe, and in the reverse direction to retract the elongate probe. Alternately or additionally, the propelling device includes an arm which grasps and pushes the probe to advance it, and grasps and pulls the probe to retract it.

Preferably, the propelling device includes a rotating mechanism, which rotates the probe about a longitudinal axis thereof. Preferably, the rotating mechanism includes rollers which roll against the elongated probe.

Preferably the propelling device includes a motor which drives the insertion of the probe.

Preferably, the propelling device includes a force sensor which measures a force applied during insertion of the elongate probe, most preferably, including a torque gauge which measures a torque required to move the elongate probe.

Preferably the control console receives force measurements from the force sensor and provides tactile feedback responsive thereto to the user.

Preferably the propelling device includes a movement sensor for measuring a linear advance of the elongate probe.

Preferably, the system includes a fluoroscope which produces a real-time image showing the progress of the elongate probe in the patient's body, which is displayed on the control console. Most preferably, the console includes a display which receives and displays data relating to the propelling device.

Preferably, the user controls includes a joystick for tactile control of the propelling device.

There is additionally provided, in accordance with a preferred embodiment of the present invention, a method for catheterization including:

inserting an elongate, flexible probe into a body passage;

feeding a portion of the probe outside the body into a propelling device, which advances the probe through the body passage; and controlling the propelling device to advance the probe from a location remote from the body.

Preferably, feeding the portion of the probe includes feeding the probe between wheels which roll against the probe to advance it. Additionally or alternately, feeding the portion of the probe includes grasping the probe with an arm which pushes the probe to advance it.

Preferably, feeding the portion of the probe includes feeding the probe into a rotating mechanism, which rotates the probe about a longitudinal axis thereof, most preferably including feeding the probe between rollers which roll against the probe to rotate the probe around its longitudinal axis.

Preferably, controlling the propelling device includes controlling a motor which drives the insertion of the elongate probe.

Preferably, controlling the propelling device includes measuring a force applied to move the elongate probe, most preferably by measuring a torque.

Preferably, controlling the propelling device includes measuring a linear advance of the elongate probe.

Preferably, controlling the propelling device includes displaying a fluoroscopic image showing progress of the elongate probe in the patient's body.

Preferably, controlling the propelling device includes receiving measurements relating to the propelling device and displaying the measurements on the control console.

Preferably, controlling the propelling device includes operating a joystick, most preferably, including receiving tactile feedback relating to the propelling device.

Preferably, inserting the elongate probe includes inserting a guide wire and inserting the elongate probe over the guide wire. Additionally or alternatively, the method includes inserting an ancillary device through the elongate probe.

Preferably, inserting the elongate probe includes inserting a catheter into a blood vessel.

In a preferred embodiment, controlling the propelling device includes controlling the device to advance the catheter to the heart.

The present invention will be more fully understood from the following detailed description of the preferred embodiments thereof, taken together with the drawings in which:

DETAILED DESCRIPTION OF PREFERRED EMBODIMENTS

Figure 1:
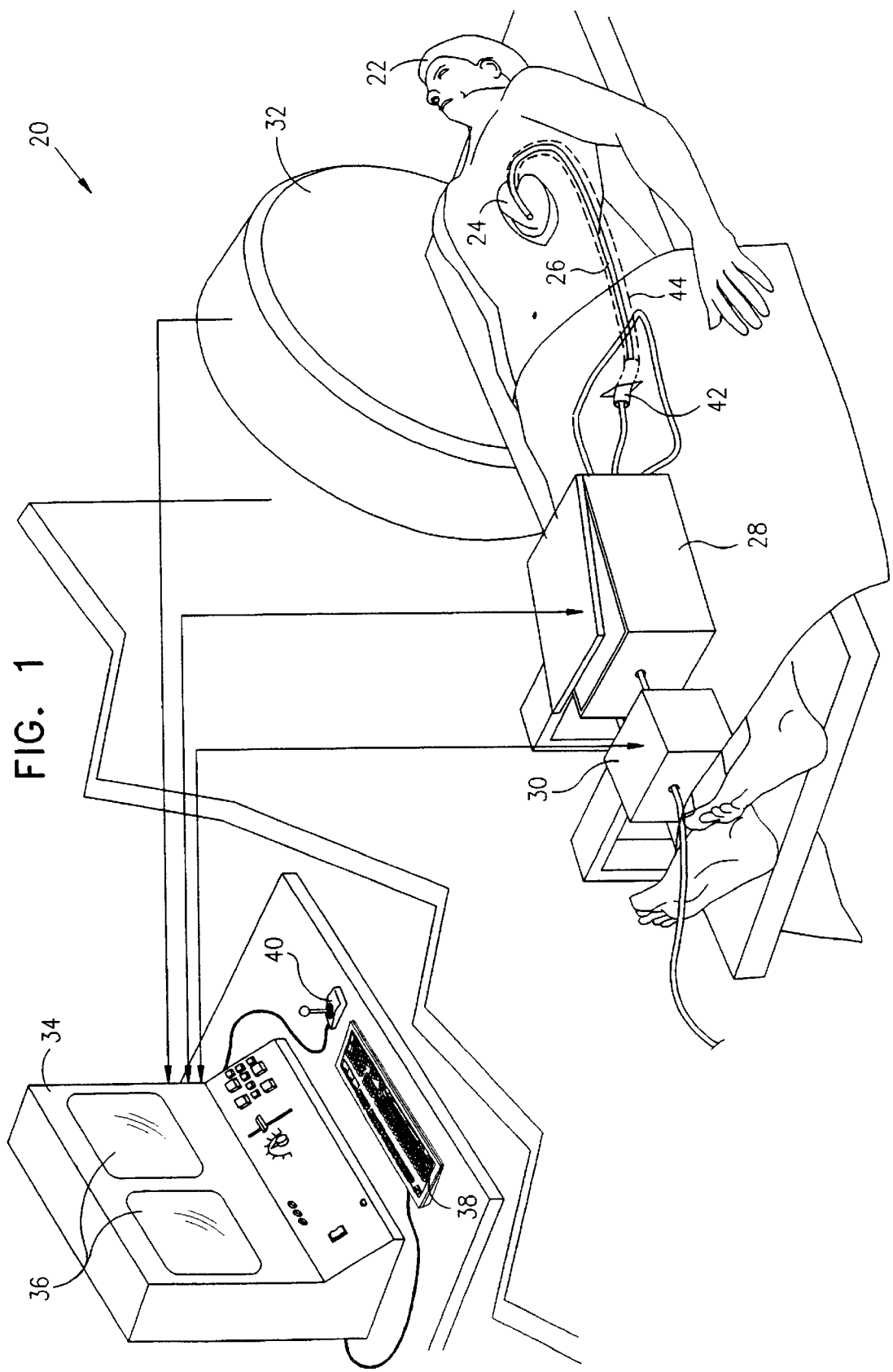
FIG. 1 is a simplified, pictorial illustration of a system for remote control catheterization, in accordance with a preferred embodiment of the present invention.

Reference is now made to FIG. 1, which is a simplified, pictorial illustration of a remote control catheterization system 20, in accordance with a preferred embodiment of the present invention. System 20 comprises a guiding catheter 26, which is fed via a cannula 42 into a blood vessel 44 leading to a target location in a vessel or a heart 24 of a patient 22. Preferably, the catheter is fed over a guide wire, which is omitted in FIG. 1 for simplicity but shown in detail in FIG. 2, below.

Catheter 26 is fed through a catheter propelling device 28, and then coupled proximally with a catheter interface 30. As shown In FIG. 1, device 28 may be opened for insertion of the catheter and other elements and, optionally, for manual override of the operation of the device, as described further hereinbelow. Interface 30 may be used to perform various therapeutic and/or diagnostic catheter procedures, such as balloon inflation or injection of contrast media, or any other such catheter-based treatments known in the art. A fluoroscope 32 is used to capture images showing the position of catheter 26 in the patient's body. (For simplicity, the X-ray tube associated with the fluoroscope is not shown in the figure.)

Propelling device 28, interface 30 and fluoroscope 32 all communicate with a control console 34. The various elements of system 20 relay operative information to console 34, and receive operative instructions from the console. Preferably, device 28 relays to console 34 force measurements associated with insertion of the catheter and an indication of the distance that the catheter has traveled; interface 30 relays applicable data from the catheter regarding the therapeutic and/or diagnostic procedures being performed; and fluoroscope 32 conveys X-ray images.

The data are preferably displayed on console 34 via a pair of displays, monitors 36. Preferably, one of monitors 36 displays fluoroscopic images, and the other monitor displays data received from propelling device 28 and interface 30. Alternatively, the data may be presented using dials, meters, or any means known and used in the art.

Console 34 also includes a user-interface peripheral device 38 and a tactile control unit 40. Medical personnel operating system 20 use device 38, preferably a keyboard, to send directional commands, for example to control table and fluoroscope motions, and to operate interface 30 and fluoroscope 32. Control unit 40, preferably a joystick with tactile and speed feedback, as described herein below, sends directional and speed instructions to propelling device 28.

In order to prevent exposure by medical staff to the fluoroscope's high levels of radiation, console 34 is preferably located outside of the catheterization room or in an area of the room that is shielded from radiation generated by the fluoroscope X-ray tube. The present invention, via this usage of remote control communication with console 34, thus furnishes the medical staff with all the relevant information, and all the relevant remote control means, to perform the catheterization operation without danger of radiation exposure.

Alternatively or additionally, console 34, or certain elements thereof, may be in a remote location, even in a different city from the patient, and communicate with the other elements of system 20 over telecommunication channels. For example, in addition to displaying images to the operating staff in a room adjacent to the catheterize operation, the same images can be relayed in parallel to medical colleagues or trainees in locations further away from the catheterization room. In yet another preferred embodiment, the present invention enables the entire catheterization procedure, including actions taken by medical staff in controlling the procedure, to be visually recorded via a visual recording device for post-operative observation or analysis.

Figure 2:
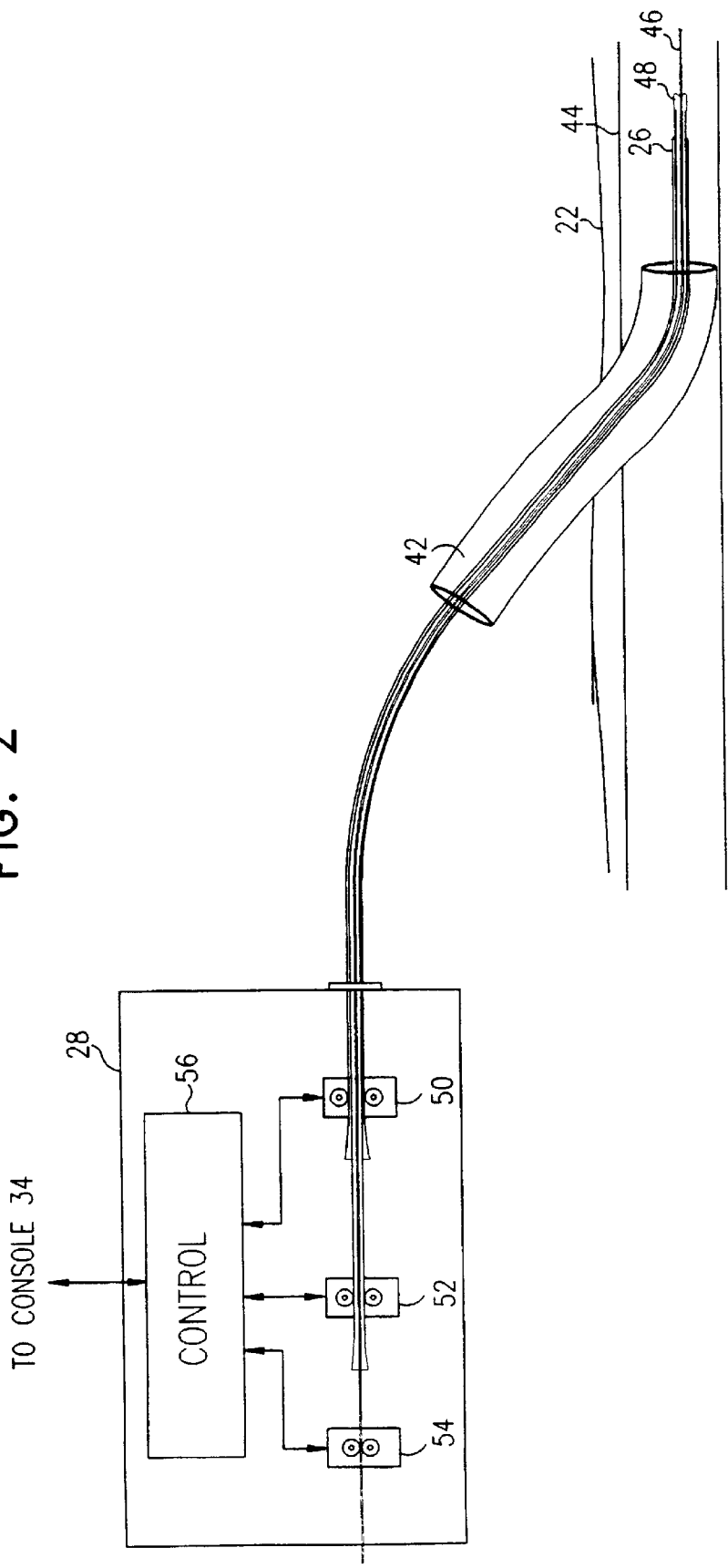
FIG. 2 is a schematic illustration of a catheter propelling device, for use in the system of FIG. 1, in accordance with a preferred embodiment of the present invention.

FIG. 2 is a schematic illustration showing details of catheter propelling device 28, for use in the system of FIG. 1, in accordance with a preferred embodiment of the present invention. As noted above with reference to FIG. 1, cannula 42 is inserted into blood vessel 44. Preferably a guide wire 46 is threaded through cannula 42 into vessel 44. Once guide wire 46 is in a desired position, catheter 26 is slipped over guide wire 46 and guided to a desired position, for example, in one of the chambers of heart 24 or in one of the coronary arteries. Once catheter 26 is in place, guide wire 46 may be withdrawn if desired. An ancillary instrument 48, such as an angioplasty balloon, may be passed through the catheter, into the heart or arteries. The guide wire, catheter and ancillary instrument are themselves substantially similar to devices of these types known in the art. The present invention provides novel apparatus and methods for inserted these devices, as well as other invasive probes and instruments known in the art.

As shown in FIG. 2, propelling device 28 comprises one or more propelling mechanisms, preferably three such mechanisms 50, 52 and 54. Propelling mechanism 50 provides the feeding force which advances catheter 26 through vessel 44. Propelling mechanism 52 provides feeding force to instrument 48, and propelling mechanism 54 provides feeding force to guide wire 46. The operation of these mechanisms is described in greater detail with reference to FIG. 3, below.

A controller 56 provides drive signals and direction to mechanisms 50, 52 and 54. Additionally, control 56 receives feedback from the mechanisms regarding the insertion force and speed of catheter 26, wire 46 or instrument 48, as applicable, as described in greater detail hereinbelow. Controller 56 is coupled in a closed loop to console 34, conveying to console 34 the force and speed feedback and receiving from console 34 instructions to be passed on to mechanisms 50, 52 and 54.

Although device 28 is preferably driven by controller 56, the medical staff may optionally halt the remote operation of device 28 by controller 56, and may manually override the operation of mechanisms 50, 52 and 54 to insert catheter 26, wire 46, or instrument 48, as applicable.

Figure 3:
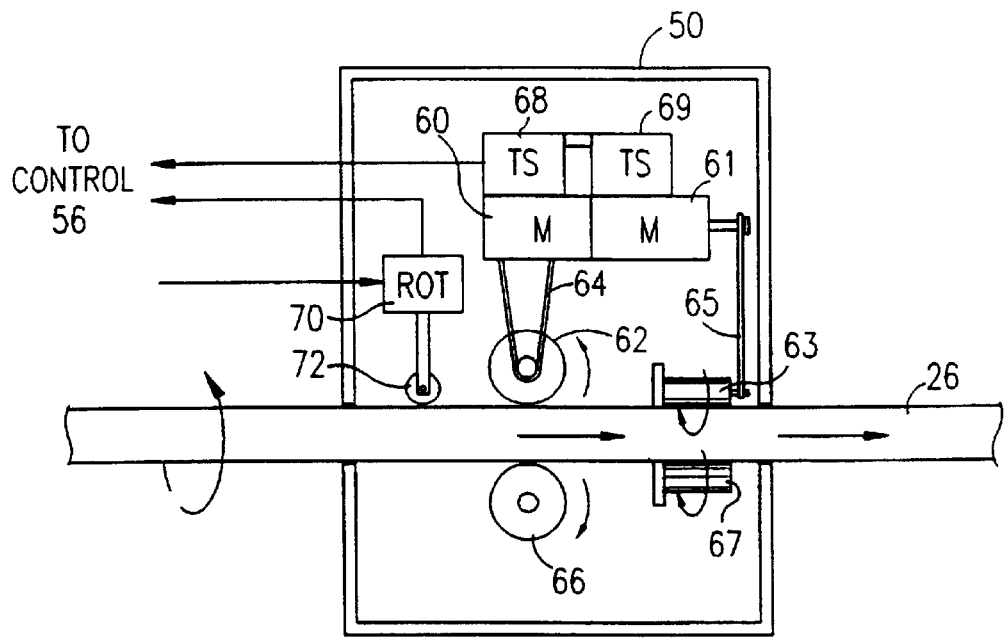
FIG. 3 is a schematic illustration showing details of a catheter propelling mechanism, for use in the propelling device of FIG. 2, in accordance with a preferred embodiment of the present invention.

FIG. 3 is a schematic illustration showing details of mechanism 50, shown in FIG. 2, in accordance with a preferred embodiment of the present invention. Mechanism 50 is described herein by way of example, and it will be understood that mechanisms 52 and 54 operate in a substantially similar manner. Furthermore, although propelling device 28 is shown in FIG. 2 as comprising three mechanisms 50, 52, and 54, for catheter 26, ancillary device 48 and guide wire 46, respectively, a single mechanism such as mechanism 50 could be used, albeit less conveniently, to advance the guide wire, catheter and ancillary device in turn.

Mechanism 50 comprises two wheels 62 and 66, which engage catheter 26 and rotate either in the forward direction, as shown by the arrows in the figure, to advance the catheter through vessel 44, or backward to retract catheter 26. Additionally, mechanism 50 preferably comprises two rollers 63 and 67 located on an axis 90° from that of wheels 62 and 66, which engage catheter 26 and rotate it around its longitudinal axis, preferably by at least ±180°, as shown by the arrows in the figure. The distance between wheels 62 and 66, and between 63 and 67, is preferably adjustable to accommodate the width of catheter 26, or of wire 46 or ancillary device 48.

A rotary motor 60, preferably a reversible stepper motor or servo motor, as are known in the art, is coupled to drive wheel 62, preferably via a belt 64. The belt is preferably coupled to motor 60 via a non-slip hub. Wheel 66, located on the opposite side of catheter 26, is preferably free turning, and rotates as driven by the motion of the catheter. In a similar manner, a rotary motor 61 is coupled to drive roller 63 via a belt 65. Roller 67, located on the opposite side of catheter 26, operates similarly to wheel 66.

Upon completion of the catheterization procedure, or whenever it is necessary to move the catheter back proximally during the procedure, the rotation of motor 60 is reversed, creating a clockwise rotation of wheel 62 and belt 64, thereby retracting catheter 26.

The force required to advance or rotate catheter 26 is monitored by a torque gauge 68 coupled to motor 60, and by a torque gauge 69 coupled to motor 61, respectively. For example, gauge 68 may measure the electrical current required by motor 60 to advance catheter 26, and translates this current to a measurement of force. The force readouts from gauges 68 and 69 are relayed to controller 56 and from there, preferably, to console 34. Alternatively, other types of force and torque sensors known in the art may also be used. When catheter 26 encounters an obstruction in vessel 44, motor 60 or motor 61 will generally require greater current to achieve forward movement or rotate, respectively. Controller 56 preferably shuts off motor 60 or 61, automatically when the current or other torque indication received by gauge 68 or 69, respectively, reaches a predetermined maximum level.

Although in the preferred embodiment shown in FIG. 3, wheel 62 and roller 63 are driven and monitored by separate, respective motors and controllers, wheel 62 and roller 63 may alternatively be driven by a common motor, with appropriate gearing, and with a single force gauge.

Mechanism 50 preferably provides an additional level of safety by the usage of a movement sensor, such as a rotor gauge 70. Rotor gauge 70 is coupled to a wheel 72 which is placed in contact with catheter 26. Preferably, rotor gauge 70 measures the number of rotations of wheel 72, thereby measuring the actual speed of movement and/or total cumulative advance of catheter 26, independent of motor 60. This information is then relayed to controller 56, which passes the information on to console 34.

As described above with reference to FIG. 1, the medical staff at console 34 are capable of remotely directing propelling device 28, through controller 56, using peripheral device 38 and tactile control unit 40. Controller 56, upon receipt of directions from console 34, changes the current levels fed to motor 60 or 61, thereby changing the speed of motor, as appropriate. Preferably, the torque measurements from torque sensor 68 are fed back to unit 40 as tactile feedback. For example, assuming unit 40 to comprise a joystick, as shown in FIG. 1, the more force needed to advance the catheter, the harder will it be to push the joystick forward to cause the catheter to advance. In addition, the torque and rotation readings, as well as other system parameters, are preferably displayed on one of displays 36, as described above.

Figure 4:
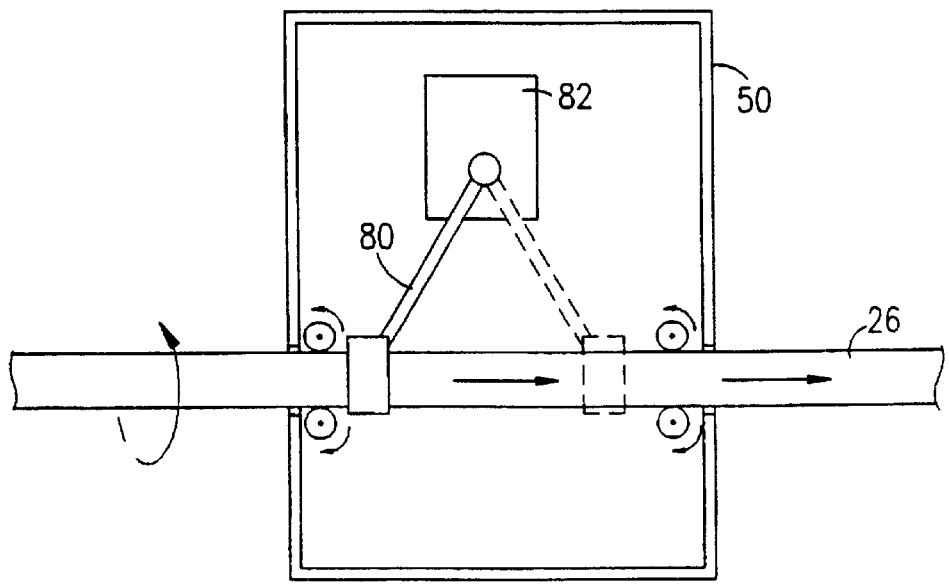
FIG. 4 is a schematic illustration showing details of a catheter propelling mechanism, in accordance with an alternative embodiment of the present invention.

FIG. 4 is a schematic illustration showing details of catheter propelling mechanism 50, in accordance with an alternative embodiment of the present invention. In this case, catheter 26 is advanced via a pushing motion and rotated via a twisting motion created by an arm 80, which is driven by a motor unit 82. All safety precautions supplied by torque gauges 68 and 69 and rotor gauge 70 are applicable to this alternate embodiment as well. The movement of arm 80 resembles the action performed by a physician in inserting a catheter by hand. Tactile control unit 40 in this preferred embodiment may also be designed so that the physician's interaction with the control unit is similar to the actions normally taken in advancing a catheter manually.

Although two preferred mechanisms for propelling catheter 26 are presented in FIGS. 3 and 4 (or for propelling guide wire 46 or ancillary device 48 as applicable), other propelling mechanisms may similarly be used. It will be appreciated generally that the preferred embodiments described above are cited by way of example, and the full scope of the invention is limited only by the claims.

What is claimed is:

1. A remote control catheterization system for coaxially inserting into the vasculature of a patient at least a first elongated probe and a second elongated probe, the system comprising:

a propelling device for controllably inserting the elongated probes, comprising at least a first mechanism for propelling the first elongated probe and a second mechanism for propelling the second elongated probe, the propelling mechanisms operating coaxially;

a control console, in communication with the propelling device, and comprising user controls which are operated by a user of the system remote from the patient to control insertion of the elongated probes into the vasculature by the propelling device;

wherein the propelling device comprises a force sensor which measures a force applied during insertion of the elongated probe, the force sensor comprises a torque gauge which measures a torque required to move the elongated probe.

2. A system according to claim 1, wherein the propelling device comprise wheels which roll against the elongated probes in one direction to advance the elongated probes, and in the reverse direction to retract the elongated probes.

3. A system according to claim 1, wherein the propelling device comprises an arm which grasps and pushes the elongated probe to advance it and grasps and pulls the elongated probe to retract it.

4. A system according to claim 1, wherein the propelling device comprises a rotation mechanism, which rotates the elongated probe about a longitudinal axis thereof.

5. A system according to claim 4, wherein the rotating mechanism comprises rollers which roll against the elongated probe.

6. A system according to claim 1, wherein the propelling device comprises a motor which drives the insertion of the elongated probe.

7. A system according to claim 1, wherein the control console receives force measurements from the force sensor and provides tactile feedback responsive thereto to the user.

8. A system according to claim 1, wherein the propelling device comprises a movement sensor for measuring a linear advance of the elongated probe.

9. A system according to claim 1, wherein the control console comprises a display which receives and displays data relating to the propelling device.

10. A system according to claim 1, wherein the user controls comprise a joystick for tactile control of the propelling device.

11. A remote control catheterization system for coaxially inserting into the vasculature of a patient at least a first elongated probe and a second elongated probe, the system comprising:

a propelling device for controllably inserting the elongated probes, comprising at least a first mechanism for propelling the first elongated probe and a second mechanism for propelling the second elongated probe, the propelling mechanisms operating coaxially;

a control console, in communication with the propelling device, and comprising user controls which are operated by a user of the system remote from the patient to control insertion of the elongated probes into the vasculature by the propelling device; wherein the system comprises a fluoroscope which produces a real-time image showing the progress of any of the elongated probes in the body of the patient.

12. A remote control catheterization method for coaxially inserting into the vasculature of a patient at least a first elongated probe and a second elongated probe, the method comprising:

provisioning a system comprising:
   a propelling device for controllably inserting the elongated probes, comprising at least a first mechanism for propelling the first elongated probe and a second mechanism for propelling the second elongated probe, the propelling mechanisms operating coaxially;
   a control console, in communication with the propelling device, and comprising user controls which are operated by a user of the system remote from the patient to control insertion of the elongated probes into the vasculature by the propelling device;
inserting the first elongated probe into a body passage of the patient;
inserting, coaxially to the first elongated probe, the second elongated probe into the same body passage;
feeding a portion of the first elongated probe into the first propelling mechanism, and a portion of the second elongated probe into the second propelling mechanism, advancing the elongated probes through the body passage; and
controlling the propelling device to advance the elongated probes from a location remote from the body;
wherein controlling the propelling device comprises measuring a force applied to move the elongated probe by measuring torque.

13. A method according to claim 12, wherein feeding the portion of the elongated probe comprises feeding the probe between wheels which roll against the probe to advance it.

14. A method according to claim 12, wherein feeding the portion of the probe comprises grasping the probe with an arm which pushes the probe to advance it.

15. A method according to claim 12, wherein feeding the portion of the probe comprises feeding the probe into a rotating mechanism which rotates the probe about a longitudinal axis thereof.

16. A method according to claim 12, wherein feeding the portion of the probe into the rotating mechanism comprises feeding the probe between rollers which roll against the probe to rotate the probe around the longitudinal axis.

17. A method according to claim 12, wherein controlling the propelling device comprises controlling a motor which drives the insertion of the elongated probe.

18. A method according to claim 12, wherein controlling the propelling device comprises measuring a linear advance of the elongated probe.

19. A method according to claim 12, wherein controlling the propelling device comprises receiving measurements relating to the propelling device and displaying the measurements on the control console.

20. A method according to claim 12, wherein controlling the propelling device comprises operating a joystick.

21. A method according to claim 20, wherein operating the joystick comprises receiving tactile feedback relating to the propelling device.

22. A method according to claim 12, wherein inserting the elongated probe comprises inserting a guide wire and inserting the elongated probe over the guide wire.

23. A method according to claim 12, wherein inserting the elongated probe comprises inserting a catheter into a blood vessel.

24. A method according to claim 23, wherein controlling the propelling device comprises controlling the device to advance the catheter to the heart.

25. A remote control catheterization method for coaxially inserting into the vasculature of a patient at least a first elongated probe and a second elongated probe, the method comprising:

providing a system comprising:
   a propelling device for controllably inserting the elongated probes, comprising at least a first mechanism for propelling the first elongated probe and a second mechanism for propelling the second elongated probe, the propelling mechanisms operating coaxially;
   a control console, in communication with the propelling device, and comprising user controls which are operated by a user of the system remote from the patient to control insertion of the elongated probes into the vasculature by the propelling device;
inserting the first elongated probe into a body passage of the patient;
inserting, coaxially to the first elongated probe, the second elongated probe into the same body passage;
feeding a portion of the first elongated probe into the first propelling mechanism, and a portion of the second elongated probe into the second propelling mechanism, advancing the elongated probes through the body passage; and
controlling the propelling device to advance the elongated probes from a location remote from the body by displaying a fluoroscopic image showing progress of the elongated probe in the patient's body.

26. A remote control catheterization method for coaxially inserting into the vasculature of a patient at least a first elongated probe and a second elongated probe, the method comprising:

providing a system comprising:
   a propelling device for controllably inserting the elongated probes, comprising at least a first mechanism for propelling the first elongated probe and a second mechanism for propelling the second elongated probe, the propelling mechanisms operating coaxially;
   a control console, in communication with the propelling device, and comprising user controls which are operated by a user of the system remote from the patient to control insertion of the elongated probes into the vasculature by the propelling device;
inserting the first elongated probe into a body passage of the patient;
inserting, coaxially to the first elongated probe, the second elongated probe into the same body passage;
inserting an ancillary device through one of said elongated probe
feeding a portion of the first elongated probe into the first propelling mechanism, and a portion of the second elongated probe into the second propelling mechanism, advancing the elongated probes through the body passage; and
controlling the propelling device to advance the elongated probes from a location remote from the body.

* * * * *

UNITED STATES PATENT AND TRADEMARK OFFICE
Certificate

Patent No. 6,726,675 B1                                                          Patented: April 27, 2004

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Dalia Beyar, Haifa (IL); and Rafael Beyar, Haifa (IL).

Signed and Sealed this Twenty-third Day of December 2008.

<div style="text-align:right">

NICHOLAS D. LUCCHESI
*Supervisory Patent Examiner*
Art Unit 3763

</div>